United States Patent [19]

Brown et al.

[11] 4,185,103

[45] Jan. 22, 1980

[54] PHARMACOLOGICALLY ACTIVE TRIAZINONES

[75] Inventors: Thomas H. Brown, Welwyn Garden City; Robert J. Ife, Stevenage, both of England

[73] Assignee: Smith Kline & French Laboratories Limited, Welwyn Garden City, England

[21] Appl. No.: 885,940

[22] Filed: Mar. 13, 1978

[30] Foreign Application Priority Data

Mar. 19, 1977 [GB] United Kingdom ............... 11757/77
Mar. 21, 1977 [GB] United Kingdom ............... 11828/77

[51] Int. Cl.$^2$ .................... C07D 253/06; A61K 31/53
[52] U.S. Cl. ..................................... 424/249; 544/182
[58] Field of Search ........................ 544/182; 424/249

[56] References Cited

U.S. PATENT DOCUMENTS 3,932,644  1/1976  Durant et al. ..................... 424/263

FOREIGN PATENT DOCUMENTS 814032 10/1974 Belgium.
846452  3/1977 Belgium.
849810  6/1977 Belgium.
168863  3/1977 Hungary.

*Primary Examiner*—John M. Ford
*Attorney, Agent, or Firm*—Joan S. Keps; Richard D. Foggio; William H. Edgerton

[57] ABSTRACT

The compounds are substituted 1,2,4-triazin-5-ones which are histamine $H_2$-antagonists. Two specific compounds of the present invention are 3-[2-(5-methyl-4-imidazolylmethylthio)ethylamino]-6-(3-methoxybenzyl)-1,2,4-triazin-5-one and 3-[2-(5-methyl-4-imidazolylmethylthio)ethylamino]-6-(3-pyridylmethyl)-1,2,4-triazin-5-one.

18 Claims, No Drawings

PHARMACOLOGICALLY ACTIVE TRIAZINONES

This invention relates to pharmacologically active compounds, to methods for preparing these compounds, to pharmaceutical compositions containing these compounds and to methods of blocking histamine $H_2$-receptors by administering these compounds. The compounds of the invention can exist as acid addition salts but, for convenience, reference will be made throughout this specification to the parent compounds.

Many physiologically active substances elicit their biological actions by interaction with specific sites known as receptors. Histamine is such a substance and has a number of biological actions. Those biological actions of histamine which are inhibited by drugs commonly called "antihistamines" of which mepyramine, diphenhydramine and chlorpheniramine are examples, are mediated through histamine $H_1$-receptors (Ash and Schild, *Brit. J. Pharmac. Chemother.*, 27, 427, (1966)), and drugs with this activity are hereinafter referred to as histamine $H_1$-antagonists. However, other of the biological actions of histamine are not inhibited by histamine $H_1$-antagonists and actions of this type which are inhibited by a compound described by Black et al. (Nature, 236, 385, (1972)) and called burimamide are mediated through receptors which are defined by Black et al. as histamine $H_2$-receptors. Thus histamine $H_2$-receptors may be defined as those histamine receptors which are not blocked by mepyramine but are blocked by burimamide. Compounds which block histamine $H_2$-receptors are referred to as histamine $H_2$-antagonists.

Blockade of histamine $H_2$-receptors is of utility in inhibiting the biological actions of histamine which are not inhibited by histamine $H_1$-antagonists. Histamine $H_2$-antagonists are therefore useful, for example, as inhibitors of gastric acid secretion, as anti-inflammatory agents and as agents which act on the cardiovascular system, for example, as inhibitors of the effects of histamine on blood pressure. In the treatment of certain conditions, for example, inflammation and in inhibiting the actions of histamine on blood pressure, a combination of histamine $H_1$- and $H_2$-antagonists is useful.

In U.S. Pat. No. 3,932,644 compounds of Formula 1 and tautomers thereof are described as histamine $H_2$-antagonists.

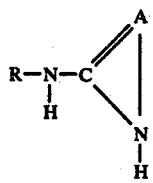

FORMULA 1

In Formula 1 A taken together with the nitrogen and carbon atoms shown forms a pyrimidine, imidazoline, quinazoline, pyridine, benzothiadiazine, 1,2,4-thiadiazine thiazoline, 1,2,4-triazine or quinoline ring, said ring having a keto, thione, or sulfone group and optionally substituted by one or two lower alkyl, phenyl or benzyl groups; R is a grouping of the structure shown in Formula 2:

FORMULA 2 wherein Het is a nitrogen containing heterocyclic ring such as imidazole, pyridine, thiazole, isothiazole or thiadiazole which ring is optionally substituted by lower alkyl preferably methyl, amino, hydroxy or halogen; Z is sulphur or a methylene group; and n is 2 or 3.

We have now found a group of compounds which are histamine antagonists and which have histamine $H_1$-antagonist activity as well as histamine $H_2$-antagonist activity.

This group of compounds which are the compounds of this invention is represented by Formula 3:

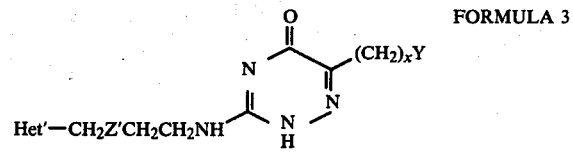

FORMULA 3 wherein Het' is a 2- or 4-imidazolyl ring optionally substituted by lower alkyl (preferably methyl), halogen (preferably chlorine or bromine), trifluoromethyl or hydroxymethyl, a 2-pyridyl ring optionally substituted by one or two groups (which may be the same or different) selected from lower alkyl (preferably methyl), lower alkoxy (preferably methoxy), halogen (preferably chlorine or bromine), amino and hydroxy, a 2-pyridyl ring with a phenyl, carbocyclic or cyclic ether ring containing 2 oxygen atoms fused to it, a 2-thiazolyl ring, a 3-isothiazolyl ring optionally substituted by chlorine or bromine, a 3-(1,2,5)-thiadiazolyl ring optionally substituted by chlorine or bromine, or a 2-(5-amino-1,3,4-thiadiazolyl) ring; Z' is sulphur or a methylene group; x is 1 to 5; Y is a 1- or 2-naphthyl ring, a 2,3-dihydro-1,4-benzodioxinyl or a 1,3-benzodioxolyl ring, a phenyl ring substituted with one or more lower alkyl, lower alkoxy, halogen, arylalkoxy (preferably benzyloxy), hydroxy, loweralkoxyloweralkoxy, trifluoromethyl, di(lower alkyl) amino, phenoxy, halophenoxy, lower alkoxyphenoxy, phenyl, halophenyl or lower alkoxyphenyl groups, a 5 or 6 membered heterocycle such as a pyridine, furan, thiophen, thiazole, oxazole, isothiazole, imidazole, pyrimidine, pyrazine or pyridazine ring, which ring is optionally substituted by lower alkyl, lower alkoxy or Y is a pyridine, imidazole or thiazole ring which has a benzene ring fused to it, or when x is other than 1, Y may also be phenyl; or a pharmaceutically acceptable salt thereof.

Preferably Het' is a 2-thiazolyl, 5-methyl-4-imidazolyl, 5-bromo-4-imidazolyl, 3-bromo-2-pyridyl, 3-chloro-2-pyridyl, 3-methoxy-2-pyridyl or 3-hydroxy-2-pyridyl ring.

Preferably Z' is sulphur.

Preferably x is 1.

Preferably Y is a phenyl group substituted by one or two lower alkoxy groups (particularly 3-methoxyphenyl, 4-methoxyphenyl or 3,4-dimethoxyphenyl), a 2,3-dihydro-1,4-benzodioxinyl ring, a 1,3-benzodioxolyl ring, or a 2-pyridyl, 3-pyridyl, 6-methyl-3-pyridyl, 4-pyridyl or 2-thiazolyl ring.

Throughout this specification by the term 'lower alkyl' we mean an alkyl group containing from 1 to 4 carbon atoms, and by the term 'lower alkoxy' we mean an alkoxy group containing from 1 to 4 carbon atoms.

The compounds of Formula 3 are described as 2H-1,2,4-triazinone derivatives and these compounds exist in equilibrium with the 4H-tautomers, and to a lesser extent as the hydroxy tautomers. The triazine ring may also exist in the following tautomeric forms:

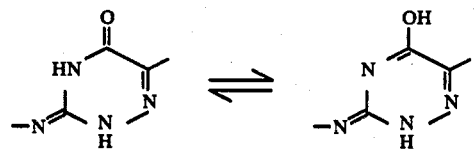

Certain Het' may also exist in several tautomeric forms, and it will be understood that all these tautomeric forms are within the scope of the present invention. Hydrates of compounds of Formula 3 and pharmaceutically acceptable hydrated salts of compounds of Formula 3 are also within the scope of this invention.

Some specific compounds which fall within the scope of the present invention are:

3-[2-(5-methyl-4-imidazolylmethylthio)ethylamino]-6-(3-methoxybenzyl)-1,2,4-triazin-5-one 3-[2-(5-methyl-4-imidazolylmethylthio)ethylamino]-6-(3-pyridylmethyl)-1,2,4-triazin-5-one 3-[2-(2-thiazolylmethylthio)ethylamino]-6-(3-methoxybenzyl)-1,2,4-triazin-5-one 3-[2-(2-thiazolylmethylthio)ethylamino]-6-(3-pyridylmethyl)-1,2,4-triazin-5-one 3-[2-(3-bromo-2-pyridylmethylthio)ethylamino]-6-(3-pyridylmethyl)-1,2,4-triazin-5-one 3-[2-(3-bromo-2-pyridylmethylthio)ethylamino]-6-(3-methoxybenzyl)-1,2,4-triazin-5-one The compounds of Formula 3 may be prepared by a process which comprises treating a triazinone of Formula 4

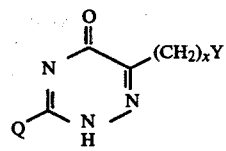

FORMULA 4 wherein x and Y are as defined in Formula 3 and Q is lower alkylthio, benzylthio or other grouping which is conveniently displaced by an amine, with an amine of formula Het'-CH$_2$-Z'-(CH$_2$)$_2$NH$_2$ wherein Het' and Z' are as defined in Formula 3. Preferably, this reaction is carried out in the absence of a solvent at an elevated temperature e.g. 150°–180° C., or in the presence of a solvent, for example, in refluxing pyridine.

The triazinones of Formula 4 wherein Q is lower alkylthio may be prepared by the following general scheme;

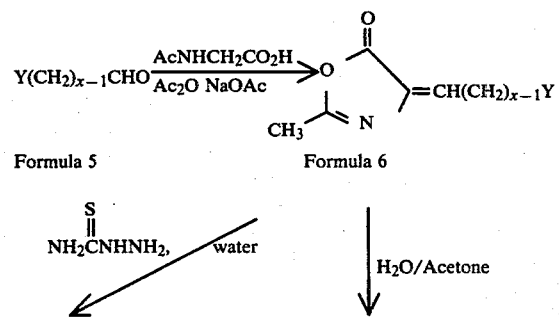

Formula 5     Formula 6

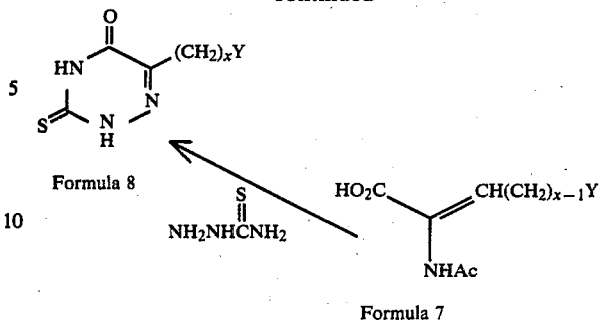

Formula 8

Formula 7 wherein a carboxaldehyde of Formula 5 is converted into an azlactone of Formula 6 which is partially hydrolysed to an acetamidoacrylic acid of Formula 7 and this is treated with thiosemicarbazide to give a compound of Formula 8, which is converted into a triazinone of Formula 4 by treatment with an alkyl halide or sulphate under alkaline conditions.

The compounds of Formula 4 wherein Q is benzylthio may be prepared by reacting a compound of Formula 8 with a benzyl halide.

Alternatively, the compounds of Formula 8 may be prepared by treating a pyruvic acid of formula Y(CH$_2$)$_{x-1}$COCO$_2$H (which may be prepared by acid hydrolysis of an azlactone of Formula 6) or an ester thereof with thiosemicarbazide and a base.

Alternatively, the compounds of Formula 8 may be prepared by treating an azlactone of Formula 6 with thiosemicarbazide in water.

The compounds of Formula 3 block histamine H$_2$-receptors, that is they inhibit the biological actions of histamine which are not inhibited by histamine H$_1$-antagonists such as mepyramine but are inhibited by burimamide. For example, the compounds of this invention have been found to inhibit histamine-stimulated secretion of gastric acid from the lumen-perfused stomachs of rats anaesthetised with urethane, at doses of from 0.5 to 16 micromoles per kilogram intravenously. This procedure is referred to in the above mentioned paper of Ash and Schild. The activity of these compounds as histamine H$_2$-antagonists is also demonstrated by their ability to inhibit other actions of histamine which, according to the above mentioned paper of Ash and Schild, are not mediated by histamine H$_1$-receptors. For example, they inhibit the actions of histamine on the isolated guinea pig atrium and isolated rat uterus.

The compounds of this invention inhibit the basal secretion of gastric acid and also that stimulated by pentagastrin or by food.

In a conventional test, such as the measurement of blood pressure in the anaesthetised cat, the action of the compounds of this invention at doses of from 0.5 to 256 micromoles per kilogram intravenously in inhibiting the vasodilator action of histamine can also be demonstrated. The level of activity of the compounds of this invention is illustrated by the effective dose producing 50% inhibition of gastric acid secretion in the anaesthetised rat (which for many of the compounds of Formula 3 is less than 10 micromoles per kilogram) and the dose producing 50% inhibition of histamine-induced tachycardia in the isolated guinea pig atrium (less than $10^{-5}$ Molar).

The compounds of Formula 3 also block histamine H$_1$-receptors, that is they inhibit the biological actions of histamine which are inhibited by mepyramine, diphenbydramine and chlorpheniramine. For example the compounds of this invention have been found to inhibit the action of histamine in the isolated guinea-pig ileum. They inhibit the histaminestimulated histamine-estimulated of the guinea-pig ileum at doses of about $10^{-5}$ Molar.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric and maleic acids and may conveniently be formed from the corresponding bases of Formula 3 by standard procedures, for example by treating the base with an acid in a lower alkanol or by the use of ion exchange resins to form the required salt either directly from the base or from a different addition salt.

Pharmaceutical compositions comprising a pharmaceutical carrier and a compound of Formula 3 or a pharmaceutically acceptable acid addition salt thereof and methods of blocking histamine $H_2$-receptors which comprise administering to an aminal a compound of Formula 3 or a pharmaceutically acceptable acid addition salt thereof are also objects of this invention. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 300 mg. If a liquid carrier is used, the preparation may be in the form of a syrup, emulsion, soft gelatin capsule, sterile injectable liquid contained for example in an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the compositions in an effective amount to block histamine $H_1$- and $H_2$-receptors. The route of administration may be oral or parenteral.

Preferably, each dosage unit will contain the active ingredient in an amount of from about 50 mg to about 250 mg.

The active ingredient will preferably be administered one to six times per day. The daily dosage regimen will preferably be from about 150 mg to about 1500 mg.

Advantageously the composition will be made up in a dosage form appropriate to the desired mode of administration for example, as a tablet, capsule, injectable solution or as a cream or ointment for topical application.

The invention is illustrated but in no way limited by the following Examples in which all temperatures are in degrees Centigrade:

EXAMPLE 1

3-[2-(5-Methyl-4-imidazolylmethylthio)ethylamino]-6-(3-methoxybenzyl)-1,2,4-triazin-5-one (i) m-Anisaldehyde (25.9 g), N-acetylglycine (15.2 g) and sodium acetate (7.8 g) were heated together under reflux in acetic anhydride (50 ml) for ¾ hour. The mixture was allowed to cool, water (150 ml) was added and the mixture was filtered to give the crude azlactone (27.7 g) m.p. 145–150°. Hydrolysis with boiling 1 N hydrochloric acid (450 ml) followed by cooling and ether extraction afforded 3-methoxyphenylpyruvic acid as a pale yellow oily solid (6.3 g).

(ii) 3-Methoxyphenylpyruvic acid (2.1 g), thiosemicarbazide (0.98 g) and sodium hydroxide (1.5 g) were heated together at 70°–75° in water (30 ml) for 1 hour. On cooling and acidification an oil was obtained which was chromatographed to give 6-(3-methoxybenzyl)-1,2,4-triazin-3-thio-3,5-dione as a pale yellow solid. Recrystallisation from ethylacetate/benzene afforded the pure product, m.p. 140°–41°.

(Found: C, 53.1; H, 4.6; N, 16.8; S, 12.6; $C_{11}H_{11}N_3O_2S$ requires: C, 53.0; H, 4.5; N, 16.9; S, 12.9%).

(iii) Sodium (0.34 g) was dissolved in ethanol (25 ml), 6-(3-methoxybenzyl)-1,2,4-triazin-3-thio-3,5-dione (3.5 g) added and the solution was cooled in ice. Methyl iodide (2.1 g) was added and the mixture was stirred at room temperature for 1 hour after which time a further quantity of methyl iodide (0.5 g) and sodium ethoxide solution (equivalent to 0.05 g sodium) was added. The mixture was cooled overnight and filtered to give 3-methylthio-6-(3-methoxybenzyl)-1,2,4-triazin-5-one (2.5 g) m.p. 185°-86°. A further quantity was obtained from the mother liquor by evaporation to dryness and treating the residue with dilute hydrochloric acid.

(iv) 3-Methylthio-6-(3-methoxybenzyl)-1,2,4-triazin-5-one (1.07 g) and 2-(5-methyl-4-imidazolylmethylthio)ethylamine (0.77 g) were heated together on an oil bath (160°–70°) for ¾ hour. The solidified mass was broken up under methanol (ca 15 ml) and boiled for 5 minutes. After cooling the white solid was filtered off and recrystallised from dimethylformamide to give the title compound as a colourless solid (0.65 g) m.p. 203°–4°.

(Found: C, 55.7; H, 5.7; N, 21.7; S, 8.3. $C_{18}H_{22}N_6O_2S$ requires: C, 55.9; H, 5.7; N, 21.8; S, 8.3%)

EXAMPLE 2

3-[2-(2-Thiazolylmethylthio)ethylamino]-6-(3-methoxybenzyl)-1,2,4-triazin-5-one

3-Methylthio-6-(3-methoxybenzyl)-1,2,4-triazin-5-one (1.18 g) and 2-(2-thiazolylmethylthio)ethylamine (0.87 g) were heated together on an oil bath (160°–70°) for ¾ hour. The resulting oil, after chromatography and crystallisation from ethanol, gave the title compound as a colourless solid (0.88 g) m.p. 128°–29°.

(Found: C, 52.4; H, 5.0; N, 18.0; S, 16.6; $C_{17}H_{19}N_5O_2S_2$ requires: C, 52.4; H, 4.9; N, 18.0; S, 16.5%).

EXAMPLE 3

3-[2-(5-Methyl-4-imidazolylmethylthio)ethylamino]-6-(3-pyridylmethyl)-1,2,4-triazin-5-one (i) Pyridine-3-carboxaldehyde (92.6 g), N-acetylglycine (86.0 g) and sodium acetate (35.3 g) were heated together under reflux in acetic anhydride (150 ml) for 1 hour. After cooling, water (250 ml) was added and the mixture was filtered to give the crude azlactone (50.9 g) m.p. 155°–60°. Partial hydrolysis of the azlactone (50 g) was achieved by heating under reflux in acetone (450 ml) and water (175 ml) for four hours. After this time the bulk of the acetone was distilled off and more water (300 ml) added. The resulting deep red solution was boiled with charcoal for 10 minutes and filtered through celite. The filtrate was evaporated to dryness and the residue was triturated and washed with acetone to give 2-acetamido-3-(3-pyridyl)acrylic acid (35 g) m.p. 191°–92° which was not further purified.

(ii) 2-Acetamido-3-(3-pyridyl)acrylic acid (10.3 g) and thiosemicarbazide (4.55 g) were heated together under reflux in water (50 ml) for 42 hours. The mixture was cooled and filtered to give 6-(3-pyridylmethyl)-1,2,4-triazin-3-thio 3,5-dione (7.22 g) m.p. ca 280° (dec.) as a pale brown solid.

(iii) Sodium (1.73 g) was dissolved in ethanol (40 ml), 6-(3-pyridylmethyl)-1,2,4-triazin-3-thio-3,5-dione (6.6 g) was added and the mixture was cooled in ice. Methyl iodide (5.0 g) was added and the mixture stirred for 30 minutes at room temperature. After evaporating to dryness the residue was taken up in water (50 ml), filtered, and the filtrate adjusted to pH 6–7 and cooled overnight. The resulting creamy solid was removed and recrystallised from methanol to give 3-methylthio-6-(3-pyridylmethyl)-1,2,4-triazin-5-one (5.86 g) m.p. 215°–16°.

(iv) 3-Methylthio-6-(3-pyridylmethyl)-1,2,4-triazin-5-one (2.34 g) and 2-(5-methyl-4-imidazolylmethylthio)-ethylamine (1.88 g) were heated together on an oil bath (160°–70°). The cooled mixture was triturated with boiling methanol and the solid was recrystallised from dimethylformamide to give the title compound as a colourless solid (2.53 g) m.p. 232°–233°.

(Found: C, 53.7; H, 5.4; N, 27.3; S, 8.8, $C_{16}H_{19}N_7OS$; requires: C, 53.8; H, 5.4; N, 27.4; S, 9.0%)

EXAMPLE 4

3-[2-(2-Thiazolylmethylthio)ethylamino]-6-(3-pyridylmethyl)-1,2,4-triazin-5-one

3-Methylthio-6-(3-pyridylmethyl)-1,2,4-triazin-5-one (3.28 g) and 2-(2-thiazolylmethylthio)ethylamine (2.7 g) were heated together on an oil bath (160°–170°) for 1 hour. The cooled mixture was triturated with isopropanol and the solid was twice recrystallised from ethanol to give the title compound as pale yellow plates (3.1 g) m.p. 158°–59°.

(Found: C, 50.0; H, 4.6; N, 23.5; S, 17.6; $C_{15}N_{16}N_6S_2O$: requires: C, 50.0; H, 4.5; N, 23.3; S, 17.8%)

EXAMPLE 5

3-[2-(3-Bromo-2-pyridylmethylthio)ethylamino]-6-(3-pyridylmethyl)-1,2,4-triazin-5-one Substitution of 2-(3-bromo-2-pyridylmethylthio)ethylamine for 2-(5-methyl-4-imidazolylmethylthio)ethylamine in the procedure of Example 3 (iv) gives the title product.

EXAMPLE 6

3-[2-(3-Bromo-2-pyridylmethylthio)ethylamino]-6-(3-methoxybenzyl)-1,2,4-triazin-5-one Substitution of 2-(3-bromo-2-pyridylmethylthio)ethylamine for 2-(5-methyl-4-imidazolylmethylthio)ethylamine in the procedure of Example 1(iv) gives the title product.

EXAMPLE 7

Substitution of the following aldehydes:
(a) Naphthalene-1-carboxaldehyde
(b) Naphthalene-2-carboxaldehyde
(c) 2,3-Dihydro-1,4-benzodioxin-6-carboxaldehyde
(d) 1,3-Benzodioxole-5-carboxaldehyde
(e) 3-Methylbenzaldehyde
(f) 4-Methoxybenzaldehyde
(g) 3,4-Dimethoxybenzaldehyde
(h) 3-Chlorobenzaldehyde
(i) 3-Benzyloxybenzaldehyde
(j) 3-Trifluoromethylbenzaldehyde
(k) 3-(Dimethylamino)benzaldehyde
(l) 3-Phenoxybenzaldehyde
(m) 3-(4-Chlorophenoxy)benzaldehyde
(n) 3-(4-Methoxyphenoxy)benzaldehyde
(o) 3-Phenylbenzaldehyde
(p) 3-(4-Chlorophenyl)benzaldehyde for m-anisaldehyde in the general procedure of Example 1 leads to the production of:

(a) 3-[2-(5-methyl-4-imidazolylmethylthio)ethylamino]-6-(1-naphthylmethyl)-1,2,4-triazin-5-one
(b) 3-[2-(5-methyl-4-imidazolylmethylthio)ethylamino]-6-(2-naphthylmethyl)-1,2,4-triazin-5-one
(c) 3-[2-(5-methyl-4-imidazolylmethylthio)ethylamino]-6-(6-(2,3-dihydro-1,4-benzodioxinyl)-1,2,4-triazin-5-one
(d) 3-[2-(5-methyl-4-imidazolylmethylthio)ethylamino]-6-(5-(1,3-benzodioxolyl)-1,2,4-triazin-5-one
(e) 3-[2-(5-methyl-4-imidazolylmethylthio)ethylamino]-6-(3-methylbenzyl)-1,2,4-triazin-5-one
(f) 3-[2-(5-methyl-4-imidazolylmethylthio)ethylamino]-6-(4-methoxybenzyl)-1,2,4-triazin-5-one
(g) 3-[2-(5-methyl-4-imidazolylmethylthio)ethylamino]-6-(3,4-dimethoxybenzyl)-1,2,4-triazin-5-one
(h) 3-[2-(5-methyl-4-imidazolylmethylthio)ethylamino]-6-(3-chlorobenzyl)-1,2,4-triazin-5-one
(i) 3-[2-(5-methyl-4-imidazolylmethylthio)ethylamino]-6-(3-benzyloxybenzyl)-1,2,4-triazin-5-one
(j) 3-[2-(5-methyl-4-imidazolylmethylthio)ethylamino]-6-(3-trifluoromethylbenzyl)-1,2,4-triazin-5-one
(k) 3-[2-(5-methyl-4-imidazolylmethylthio)ethylamino]-6-(3-(dimethylamino)benzyl)-1,2,4-triazin-5-one
(l) 3-[2-(5-methyl-4-imidazolylmethylthio)ethylamino]-6-(3-phenoxybenzyl)-1,2,4-triazin-5-one
(m) 3-[2-(5-methyl-4-imidazolylmethylthio)ethylamino]-6-(3-(4-chlorophenoxy)benzyl)-1,2,4-triazin-5-one
(n) 3-[2-(5-methyl-4-imidazolylmethylthio)ethylamino]-6-(3-(4-methoxyphenoxy)benzyl)-1,2,4-triazin-5-one
(o) 3-[2-(5-methyl-4-imidazolylmethylthio)ethylamino]-6-(3-phenylbenzy)-1,2,4-triazin-5-one
(p) 3-[2-(5-methyl-4-imidazolylmethylthio)ethylamino]-6-(3-(4-chlorophenyl)benzyl)-1,2,4-triazin-5-one

EXAMPLE 8

Treatment of 3-[2-(5-methyl-4-imidazolylmethylthio)ethylamino]-6-(3-methoxybenzyl)-1,2,4triazin-5-one with an excess of boron tribromide leads to the production of 3-[2-(5-methyl-4-imidazolylmethylthio)ethylamino]-6-(3-hydroxybenzyl)-1,2,4-triazin-5-one.

EXAMPLE 9

Substitution of 3-(methoxymethoxy)benzaldehyde for pyridine-3-carboxaldehyde in the procedure of Example 3 leads to the production of 3-[2-(5-methyl-4-imidazolylmethylthio)ethylamino]-6-(3-methoxymethoxybenzyl)-1,2,4-triazin-5-one.

EXAMPLE 10

Substitution of
(a) furan-2-carboxaldehyde
(b) thiophene-2-carboxaldehyde
(c) thiazole-2-carboxaldehyde
(d) oxazole-2-carboxaldehyde
(e) isothiazole-3-carboxaldehyde
(f) pyrimidine-2-carboxaldehyde
(g) pyrimidine-5-carboxaldehyde
(h) pyrazine-2-carboxaldehyde
(i) pyridazine-4-carboxaldehyde
for m-anisaldehyde in the general procedure of Example 1 leads to the production of
(a) 3-[2-(5-methyl-4-imidazolylmethylthio)ethylamino]-6-(2-furylmethyl)-1,2,4-triazin-5-one
(b) 3-[2-(5-methyl-4-imidazolylmethylthio)ethylamino]-6-(2-thienylmethyl)-1,2,4-triazin-5-one
(c) 3-[2-(5-methyl-4-imidazolylmethylthio)ethylamino]-6-(2-thiazolylmethyl)-1,2,4-triazin-5-one
(d) 3-[2-(5-methyl-4-imidazolylmethylthio)ethylamino]-6-(2-oxazolylmethyl)-1,2,4-triazin-5-one
(e) 3-[2-(5-methyl-4-imidazolylmethylthio)ethylamino]-6-(3-isothiazolymethyl)-1,2,4-triazin-5-one
(f) 3-[2-(5-methyl-4-imidazolylmethylthio)ethylamino]-6-(2-pyrimidylmethyl)-1,2,4-triazin-5-one
(g) 3-[2-(5-methyl-4-imidazolylmethylthio)ethylamino]-6-(5-pyrimidylmethyl)-1,2,4-triazin-5-one
(h) 3-[2-(5-methyl-4-imidazolylmethylthio)ethylamino]-6-(2-pyrazylmethyl)-1,2,4-triazin-5-one
(i) 3-[2-(5-methyl-4-imidazolylmethylthio)ethylamino]-6-(4-pyridazylmethyl)-1,2,4-triazin-5-one

EXAMPLE 11

Substitution of 1-(4-methoxybenzyl)-2-imidazole carboxaldehyde for m-anisaldehyde in the general procedure of Example 1 leads to the production of 3-[2-(5-methyl-4-imidazolylmethylthio)ethylamino]-6-(1-(4-methyoxybenzyl)-2-imidazolylmethyl)-1,2,4-triazin-5-one, which when treated with anisole and hydrogen bromide in acetic acid gives 3-[2-(5-methyl-4-imidazolylmethylthio)ethylamino]-6-(2-imidazolylmethyl)-1,2,4-triazin-5-one

EXAMPLE 12

Substitution of 2-oxo-4-phenylbutyric acid for 3-methoxyphenylpyruvic acid in the general procedure of Example 1 (ii-iv) leads to the production of 3-[2-(5-methyl-4-imidazolylmethylthio)ethylamino]-6-(3-phenylpropyl)-1,2,4-triazin-5-one

EXAMPLE 13

Substitution of
(a) 2-(2-imidazolylmethylthio)ethylamine
(b) 2-(4-imidazolymethylthio)ethylamine
(c) 2-(5-bromo-4-imidazolylmethylthio)ethylamine
(d) 2-(5-trifluoromethyl-4-imidazolylmethylthio)ethylamine
(e) 2-(5-hydroxymethyl-4-imidazolylmethylthio)ethylamine
(f) 2-(2-pyridylmethylthio)ethylamine
(g) 2-(3-methyl-2-pyridylmethylthio)ethylamine
(h) 2-(3-methoxy-2-pyridylmethylthio)ethylamine
(i) 2-(3-chloro-2-pyridylmethylthio)ethylamine
(j) 2-(3-amino-2-pyridylmethylthio)ethylamine
(k) 2-(3-hydroxy-2-pyridylmethylthio)ethylamine
(l) 2-(3-isothiazolylmethylthio)ethylamine
(m) 2-(4-bromo-3-isothiazolylmethylthio)ethylamine
(n) 2-(3-(1,2,5)-thiadiazolylmethylthio)ethylamine
(o) 2-(4-chloro-3-(1,2,5)-thiadiazolylmethylthio)ethylamine
(p) 2-(5-amino-2-(1,3,4)-thiadiazolylmethylthio)ethylamine
for 2-(5-methyl-4-imidazolylmethylthio)ethylamine in the procedure of Example 3 (iv) leads to the production of:
(a) 3-[2-(2-imidazolylmethylthio)ethylamino]-6-(3-pyridylmethyl)-1,2,4-triazin-5-one
(b) 3-[2-(4-imidazolylmethylthio)ethylamino]-6-(3-pyridylmethyl)-1,2,4-triazin-5-one
(c) 3-[2-(5-bromo-4-imidazolylmethylthio)ethylamino]-5-(3-pyridylmethyl)-1,2,4-triazin-5-one
(d) 3-[2-(5-trifluoromethyl-4-imidazolylmethylthio)ethylamine]-6-(3-pyridylmethyl)-1,2,4-triazin-5-one
(e) 3-[2-(5-hydroxymethyl-4-imidazolylmethylthio)ethylamino]-6-pyridylmethyl)-1,2,4-triazin-5-one
(f) 3-[2-(2-pyridylmethylthio)ethylamino]-6-(3-pyridylmethyl)-1,2,4-triazin-5-one
(g) 3-2-(3-methyl-2-pyridylmethylthio)ethylamino]-6-(3-pyridylmethyl)-1,2,4-triazin-5-one
(h) 3-[2-(3-methoxy-2-pyridylmethylthio)ethylamino]-6-(3-pyridylmethyl)-1,2,4-triazin-5-one
(i) 3-[2-(3-chloro-2-pyridylmethylthio)ethylamino]-6-(3-pyridylmethyl)-1,2,4-triazin-5-one
(j) 3-[2-(3-amino-2-pyridylmethylthio)ethylamino]-6-(3-pyridylmethyl)-1,2,4-triazin-5-one
(k) 3-[-(3-hydroxy-2-pyridylmethylthio)ethylamino]-6-(3-pyridylmethyl)-1,2,4-triazin-5-one
(l) 3-[2-(3-isothiazolylmethylthio)ethylamino]-6-(3-pyridylmethyl)-1,2,4-triazin-5-one
(m) 3-[2-(4-bromo-3-isothiazolylmethylthio)ethylamino]-6-(3-pyridylmethyl)-1,2,4-triazin-5-one
(n) 3-[2-(3-(1,2,5)-thiadiazolylmethylthio)ethylamino]-6-(3-pyridylmethyl)-1,2,4-triazin-5-one
(o) 3-[2-(4-chloro-3-(1,2,5)-thiadiazolylmethylthio)ethylamino]-6-(3-pyridylmethyl)-1,2,4-triazin-5-one
(p) 3-[2-(5-amino-2-(1,3,4)-thiadiazolylmethylthio)ethylamino]-6-(3-pyridylmethyl)-1,2,4-triazin-5-one

EXAMPLE 14

(i) Reaction of 2-chloro-3-nitropyridine with 2-(2-cyanoethyl)malonic acid diethyl ester and sodium hydride in tetrahydrofuran gives 1-(3-nitro-2-pyridyl)-1,1-bis-(carbethoxy)-butyronitrile, m.p. 93,5°–94.5°, which after alkaline hydrolysis and acidification gives 2-(3-cyanopropyl)-3-nitropyridine hydrochloride m.p.

142°–145.5°. Reduction with hydrogen and palladium on charcoal gives 3-amino-2-(3-cyanopropyl)pyridine, and treatment of this with sodium nitrite and sulphuric acid and subsequent warming gives 2-(3-cyanopropyl)-3-hydroxypyridine. Methylation with methyl iodide and sodium ethoxide in dimethylsulphoxide and subsequent reduction with lithium aluminium hydride gives 4-(3-methoxy-2-pyridyl)butylamine. Reduction of 3-amino-2-(3-cyanopropyl)-3-hydroxypyridine with lithium aluminium hydride gives 4-(3-amino-2-pyridyl)-butylamine. Diazotisation of 4-(3-amino-2-pyridyl)-butylamine at pH 1 and treatment with cuprous chloride or cuprous bromide gives 4-(3-chloro-2-pyridyl)-butylamine and 4-(3-bromo-2-pyridyl)-butylamine, respectively.

(ii) Substitution of
  (a) 4-(4-imidazolyl)butylamine
  (b) 4-(3-methoxy-4-pyridyl)-butylamine
  (c) 4-(3-chloro-2-pyridyl)-butylamine
  (d) 4-(3-bromo-2-pyridyl)butylamine
  (e) 4-(3-amino-2-pyridyl)butylamine
for 2-(5-methyl-4-imidazolylmethylthio)ethylamine in the procedure of Example 3(iv) leads to the production of
  (a) 3-[4-(4-imidazolyl)butylamino]-6-(3-pyridylmethyl)-1,2,4-triazin-5-one
  (b) 3-[4-(3-methoxy-2-pyridyl)butylamino]-6-(3-pyridylmethyl)-1,2,4-triazin-5-one
  (c) 3-[4-(3-chloro-2-pyridyl)butylamino]-6-(3-pyridylmethyl)-1,2,4-triazin-5-one
  (d) 3-[4-(3-bromo-2-pyridyl)butylamino]-6-(3-pyridylmethyl)-1,2,4-triazin-5-one
  (e) 3-[4-(3-amino-2-pyridyl)butylamino]-6-(3-pyridylmethyl)-1,2,4-triazin-5-one

EXAMPLE 15

Treatment of a solution of 3-[2-(5-methyl-4-imidazolyl-methylthio)ethylamino]-6-(3-methoxybenzyl)-1,2,4-triazin-5-one with two equivalents of (a) hydrochloric acid (b) hydrobromic acid or (c) sulphuric acid leads to the production of
  (a) 3-[2-(5-methyl-4-imidazolylmethylthio)ethylamino]-6-(3-methoxybenzyl)-1,2,4-triazinone dihydrochloride.
  (b) 3-[2-(5-methyl-4-imidazolylmethylthio)ethylamino]-6-(3-methoxybenzyl)-1,2,4-triazinone dihydrobromide.
  (c) 3-[2-(5-methyl-4-imidazolylmethylthio)ethylamino]-6-(3-methoxybenzyl)-1,2,4-triazinone sulphate

EXAMPLE 16

Substitution of the following aldehydes:
  (a) 3-methoxybenzaldehyde
  (b) 6-methyl-3-pyridinecarboxaldehyde
for m-anisaldehyde in the general procedure of Example 1 leads to the production of:
  (a) 3-[2-(5-methyl-4-imidazolylmethylthio)ethylamino]-6-(3-methoxybenzyl)-1,2,4-triazin-5-one
  (b) 3-[2-(5-methyl-4-imidazolylmethylthio)ethylamino]-6-(6-methyl-3-pyridylmethyl)-1,2,4-triazin-5-one

EXAMPLE 17

Substitution of the following aldehydes:
  (a) 2-(2-furyl)acetaldehyde
  (b) 3-(5-methyl-2-furyl)propionaldehyde
  (c) 2-(2-pyridyl)acetaldehyde
  (d) 4-(2-pyridyl)butyraldehyde
for m-anisaldehyde in the general procedure of Example 1 leads to the productin of:
  (a) 3-[2-(5-methyl-4-imidazolylmethylthio)ethylthio)ethylamino]-6-(2-(2-furyl)ethyl)-1,2,4-triazin-5-one
  (b) 3-[2-(5-methyl-4-imidazolylmethylthio)ethylamino]-6-(3-(5-methyl-2-furyl)propyl)-1,2,4-triazin-5-one
  (c) 3-[2-(5-methyl-4-imidazolylmethylthio)ethylamino]-6-(2-(2-pyridyl)ethyl)-1,2,4-triazin-5-one
  (d) 3-[2-(5-methyl-4-imidazolylmethylthio)ethylamino]-6-(4-(2-pyridyl)butyl-1,2,4-triazin-5-one

EXAMPLE 18

Substitution of the following aldehydes:
  (a) 2-(phenyl)propionaldehyde
  (b) 4-(phenyl)butyraldehyde
  (c) 5-(phenyl)valeraldehyde
for m-anisaldehyde in the general procedure of Example 1 leads to the production of:
  (a) 3-[2-(5-methyl-4-imidazolylmethylthio)ethylamino]-6-(2-phenylethyl)-1,2,4-triazin-5-one
  (b) 3-[2-(5-methyl-4-imidazolylmethylthio)ethylamino]-6-(4-phenylbutyl)-1,2,4-triazin-5-one
  (c) 3-[2-(5-methyl-4-imidazolylmethylthio)ethylamino]-6-(5-phenylpentyl)-1,2,4-triazin-5-one

EXAMPLE 19

Reaction of
  (a) 3-bromo-2-hydroxymethyl-4-methylpyridine
  (b) 4-hydroxymethyl-(1,3)-dioxolo[4,5-C]pyridine
  (c) 2,3-dihydro-5-hydroxymethyl (p-dioxino-[2,3-C]pyridine)
  (d) 3,4-dimethoxy-2-hydroxymethylpyridine
  (e) 5,6,7,8-tetrahydro-1-(hydroxymethyl)-isoquinoline
  (f) 1-(hydroxymethyl) isoquinoline
with cysteamine hydrobromide in hydrobromic acid gives the corresponding 2-aminoethylthiomethyl derivatives which may be substituted for 2-(5-methyl-4-imidazolylmethylthio)-ethylamine in the procedure of Example 1 (iv) to give:
  (a) 3-[2-(3-bromo-4-methyl-2-pyridylmethylthio)ethylamino]-6-(3-methoxybenzyl)-1,2,4-triazin-5-one
  (b) 3-[2-(4-(1,3-dioxolo [4,5-C]pyridyl)methylthio)-ethylamino]-6-(3-methoxybenzyl)-1,2,4-triazin-5-one
  (c) 3-[2-(5-(2,3-dihydro-p-dioxino[2,3-C]pyridyl)methylthio)ethylamino]-6-(3-methoxybenzyl)-1,2,4-triazin-5-one
  (d) 3-[2-(3,4-dimethoxy-2-pyridylmethylthio)ethylamino]-6-(3-methoxybenzyl)-1,2,4-triazin-5-one
  (e) 3-[2-(5,6,7,8-tetrahydro-1-isoquinolylmethylthio)-ethylamino]-6-(3-methoxybenzyl)-1,2,4-triazin-5-one

EXAMPLE 20

Substitution of
  (a) 4-isoquinolinecarboxaldehyde
  (b) 2-benzimidazolecarboxaldehyde
  (c) 2-benzthiazolecarboxaldehyde for m-anisaldehyde in the general procedure of Example 1 leads to the production of:
  (a) 3-[2-(5-methyl-4-imidazolylmethylthio)ethylamino]-6-(4-isoquinolylmethyl)-1,2,4-triazin-5-one
  (b) 3-[2-(5-methyl-4-imidazolylmethylthio)ethylamino]-6-(2-benzimidazolylmethyl)-1,2,4-triazin-5-one
  (c) 3-[2-(5-methyl-4-imidazolylmethylthio)ethylamino]-6-(2-benzthiazolylmethyl)-1,2,4-triazin-5-one

EXAMPLE 21

Pharmaceutical composition:

| Ingredients | Amounts |
| --- | --- |
| 3-[2-(5-methyl-4-imidazolylmethylthio)-ethylamino]-6-(3-methoxybenzyl)-1,2,4-triazinone | 100 mg |
| Sucrose | 100 mg |
| Starch | 30 mg |
| Talc | 7 mg |
| Stearic Acid | 2 mg |

The ingredients are screened, mixed and filled into a hard gelatin capsule.

EXAMPLE 22

Pharmaceutical composition:

| Ingredients | Amounts |
| --- | --- |
| 3-[2-(5-methyl-4-imidazolylmethylthio)-ethylamino]-6-(3-methoxybenzyl)-1,2,4-triazinone | 150 mg |
| Lactose | 100 mg |

The ingredients are screened, mixed and filled into a hard gelatin capsule.

Similarly, the outer compounds of Formula 3 may be formulated into pharmaceutical compositions by the procedures of Examples 21 and 22.

The pharmaceutical compositions prepared in the foregoing examples are administered to a subject within the dose ranges given hereabove to block histamine $H_1$- and $H_2$- receptors.

We claim:
1. A compound of the formula:

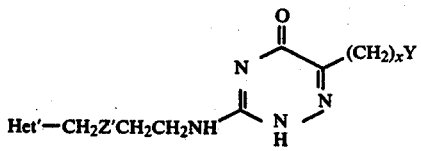

wherein Het' is a 2- or 4-imidazolyl ring optionally substituted by lower alkyl, halogen, trifluoromethyl or hydroxymethyl, a 2-pyridyl ring optionally substituted by one or two groups selected from lower alkyl, lower alkoxy, halogen, amino and hydroxy, a 2-pyridyl ring with a phenyl, carbocyclic or cyclic ether ring containing 2 oxygen atoms fused to it, a 2-thiazolyl ring, a 3-isothiazolyl ring optionally substituted by chlorine or bromine, a 3-(1,2,5)-thiadiazolyl ring optionally substituted by chlorine or bromine, or a 2-(5-amino-1,3,4-thiadiazolyl)ring; Z' is sulphur or a methylene group; x is 1 to 5; Y is a 1- or 2-naphthyl ring, a 2,3-dihydro-1,4-benzodioxinyl or a 1,3-benzodioxolyl ring, a phenyl ring substituted with one or more lower alkyl, lower alkoxy, halogen, benzyloxy, hydroxy, loweralkoxyloweralkoxy, trifluoromethyl, di(lower alkyl)amino, phenoxy, halophenoxy, lower alkoxyphenoxy, phenyl, halophenyl or lower alkoxyphenyl groups, a 5 or 6 membered heterocycle selected from the group consisting of a pyridine, furan, thiophen, thiazole, oxazole, isothiazole, imidazole, pyrimidine, pyrazine or pyridazine ring, which ring is optionally substituted by lower alkyl, lower alkoxy, or Y is a pyridine, imidazole or thiazole ring which has a benzene ring fused to it, or when x is other than 1, Y may also be phenyl; or a pharmaceutically acceptable salt thereof.

2. A compound according to claim 1 wherein Het' is a 2- or 4-imidazolyl ring optionally substituted by lower alkyl, halogen, trifluoromethyl or hydroxymethyl, a 2-pyridyl ring optionally substituted by lower alkyl, lower alkoxy, halogen, amino or hydroxy, a 2-thiazolyl ring, a 3-isothiazolyl ring optionally substituted by chlorine or bromine, a 3-(1,2,5)-thiadiazolyl ring optionally substituted by chlorine or bromine, or a 2-(5-amino-1,3,4-thiadiazolyl) ring.

3. A compound of claim 1 wherein Het' is a 2-thiazolyl, 5-methyl-4-imidazolyl, 5-bromo-4-imidazolyl, 3-bromo-2-pyridyl, 3-chloro-2-pyridyl, 3-methoxy-2-pyridyl or 3-hydroxy-2-pyridyl ring.

4. A compound of claim 1 wherein Z' is sulphur.

5. A compound of claim 1 wherein x is 1.

6. A compound of claim 1 wherein Y is a phenyl group substituted by one or two lower alkoxy groups, a 2,3-dihydro-1,4-benzodioxinyl ring, a 1,3-benzodioxolyl ring, or a 2-pyridyl, 3-pyridyl, 4-pyridyl or 2-thiazolyl ring.

7. A compound of claim 1 wherein Y is a 3-methoxyphenyl, 4-methoxyphenyl, 3,4-dimethoxyphenyl or 6-methyl-3-pyridyl.

8. A compound of claim 1, said compound being 3-[2-(5-methyl-4-imidazolylmethylthio)ethylamino]-6-(3-methoxybenzyl)-1,2,4-triazin-5-one.

9. A compound of claim 1, said compound being 3-[2-(5-methyl-4-imidazolylmethylthio)ethylamino]-6-(3-pyridylmethyl)-1,2,4-trizin-5-one.

10. A compound of claim 1, said compound being 3-[2-(2-thiazolylmethylthio)ethylamino]-6-(3-methoxybenzyl)-1,2,4-triazi-5-one.

11. A compound of claim 1, said compound being 3-[2-(2-thiazolylmethylthio)ethylamino]-6-(3-pyridylmethyl)-1,2,4-triazin-5-one.

12. A compund of claim 1, said compound being 3-[2-(3-bromo-2-pyridylmethylthio)ethylamino]-6-(3-pyridylmethyl)-1,2,4-triazin-5-one.

13. A compound of claim 1, said compound being 3-[2-(3-bromo-2-pyridylmethylthio)ethylamino]-6-(3-methoxybenzyl)-1,2,4-triazin-5-one.

14. A pharmaceutical composition comprising a compound of claim 1 in combination with a pharmaceutically acceptable diluent or carrier.

15. A pharmaceutical composition according to claim 14 in dosage unit form adapted for oral administration.

16. A pharmaceutical composition according to claim 14 comprising 3-[2-(5-methyl-4-imidazolylmethylthio)ethylamino]-6-(3-methoxybenzyl)-1,2,4-triazin-5-one in combination with a pharmaceutically acceptable diluent or carrier.

17. A method of blocking histamine $H_2$-receptors which comprises administering to an animal a compound of claim 1.

18. A method of simultaneously blocking histamine $H_1$-receptors and histamine $H_2$-receptors which comprises administering to an animal a compound of claim 1.

* * * * *